United States Patent
Tilmont et al.

(10) Patent No.: US 11,911,527 B2
(45) Date of Patent: Feb. 27, 2024

(54) REACTIVE OXYGEN SPECIES (ROS) ENHANCED ANTIBACTERIAL LIGHT SYSTEM

(71) Applicant: B/E AEROSPACE, INC., Winston Salem, NC (US)

(72) Inventors: Daniel Tilmont, Rocky Point, NY (US); Eric Johannessen, Holbrook, NY (US); John Edquist, Miwaukee, WI (US)

(73) Assignee: B/E AEROSPACE, INC., Winston Salem, NC (US)

( * ) Notice: Subject to any disclaimer, the term of this patent is extended or adjusted under 35 U.S.C. 154(b) by 327 days.

(21) Appl. No.: 17/184,913

(22) Filed: Feb. 25, 2021

(65) Prior Publication Data

US 2022/0062467 A1 Mar. 3, 2022

Related U.S. Application Data

(60) Provisional application No. 63/070,791, filed on Aug. 26, 2020.

(51) Int. Cl.
*A61L 2/10* (2006.01)
*A61L 2/08* (2006.01)
(Continued)

(52) U.S. Cl.
CPC .............. *A61L 2/10* (2013.01); *A61L 2/084* (2013.01); *A61L 2/22* (2013.01); *A61L 2/26* (2013.01);
(Continued)

(58) Field of Classification Search
CPC .......... A61L 2/10; A61L 2202/11; A61L 2/22; A61L 9/14; A61L 2209/211; A61L 2202/25
See application file for complete search history.

(56) References Cited

U.S. PATENT DOCUMENTS

| 2006/0140817 A1 | 6/2006 | Cumberland et al. |
| 2015/0209459 A1* | 7/2015 | Kreitenberg ............. A61L 2/10 250/492.1 |

(Continued)

FOREIGN PATENT DOCUMENTS

| DE | 102007037984 | 2/2009 | |
| WO | WO-2007087709 A1 * | 8/2007 | ............. A61L 2/202 |

(Continued)

OTHER PUBLICATIONS

Catherine E. Bayliss, et al., "The Synergistic Killing of Spores of Bacillus Subtilis by Hydrogen Peroxide and Ultra-Violet Light Irradiation", https://academic.oup.com/femsle/article-abstract/5/5/331/442930, Elsevier/North-Holland Biomedical Press, FEMS Microbiology Letters, vol. 5, Issue 5, 1979, pp. 331-333.

(Continued)

*Primary Examiner* — Sean E Conley
*Assistant Examiner* — Justin Hwang
(74) *Attorney, Agent, or Firm* — SNELL & WILMER L.L.P.

(57) ABSTRACT

A sanitization system for an aircraft cabin may comprise: a cabin of an aircraft; a light system including a lighting unit configured to emit an electromagnetic radiation output between 300 and 430 nanometers ("nm"); an external reactive oxygen species (ROS) generator in fluid communication with the cabin, wherein the sanitization system is configured to disinfect a target area of the cabin by targeting the target area with the electromagnetic radiation output and the ROS.

17 Claims, 6 Drawing Sheets

(51) Int. Cl.
    *A61L 2/22*     (2006.01)
    *A61L 2/26*     (2006.01)
    *A61L 9/14*     (2006.01)

(52) U.S. Cl.
    CPC ............ *A61L 9/14* (2013.01); *A61L 2202/11* (2013.01); *A61L 2202/14* (2013.01); *A61L 2202/25* (2013.01); *A61L 2209/11* (2013.01); *A61L 2209/16* (2013.01); *A61L 2209/211* (2013.01)

(56) References Cited

U.S. PATENT DOCUMENTS

| | | | |
|---|---|---|---|
| 2018/0214591 A1 | 8/2018 | Park et al. | |
| 2018/0369434 A1* | 12/2018 | Callahan | A61L 2/24 |
| 2019/0030195 A1* | 1/2019 | Hatti | A61L 2/24 |
| 2019/0247529 A1* | 8/2019 | Shane | A61L 2/208 |
| 2020/0230271 A1* | 7/2020 | Choi | F21V 1/20 |
| 2020/0254122 A1* | 8/2020 | Starkweather | A61L 2/10 |

FOREIGN PATENT DOCUMENTS

| | | | |
|---|---|---|---|
| WO | 2019068189 | 4/2019 | |
| WO | WO-2019068189 A1 * | 4/2019 | A61L 2/10 |

OTHER PUBLICATIONS

EPO; European Search Report dated Jan. 17, 2022 in Application No. 21193234.8.

\* cited by examiner

```
                600

602     Determine, by the processor, a desired target area for
             bacterial or viral disinfection 604     Command, by a processor, a light in a light system to emit
             a light output having a wavelength between about 300
             nm and 430 nm 606     Command, by the processor, a reactive oxygen species
             (ROS) to be dispensed into an aircraft cabin 608     Command, by the processor, the light and the ROS to
             target the desired target area 610     Receive, by the processor, an ROS concentration within
             the cabin 612     Modulate, by the processor and through the ROS
             generator, the ROS concentration
```

FIG. 6

REACTIVE OXYGEN SPECIES (ROS) ENHANCED ANTIBACTERIAL LIGHT SYSTEM

CROSS-REFERENCE TO RELATED APPLICATIONS

This application is a non-provisional of, and claims priority to, and the benefit of U.S. Provisional Application No. 63/070,791, entitled "REACTIVE OXYGEN SPECIES (ROS) ENHANCED ANTIBACTERIAL LIGHT SYSTEM," filed on Aug. 26, 2020, which is hereby incorporated by reference in its entirety.

FIELD

The present disclosure relates generally to light systems and, more particularly, to reactive oxygen species (ROS) enhanced antibacterial light systems for aircrafts.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization system for an aircraft cabin is disclosed herein. The sanitization system may comprise: a cabin of an aircraft; a light system including a lighting unit configured to emit an electromagnetic radiation output between 300 and 430 nanometers ("nm"); an external reactive oxygen species (ROS) generator in fluid communication with the cabin, wherein the sanitization system is configured to disinfect a target area of the cabin by targeting the target area with the electromagnetic radiation output and the ROS.

In various embodiments, the ROS produced by the external ROS generator is hydrogen peroxide or ozone. The ROS may be an aerosolized hydrogen peroxide. The sanitization system may further comprise an air handler in fluid communication with the cabin, wherein the external reactive oxygen species (ROS) is in fluid communication with the air handler. The lighting unit may further comprise: a first light-emitting diode ("LED") configured to emit a first electromagnetic radiation output between 600 and 740 nm; a second LED configured to emit a second electromagnetic radiation output between 500 and 565 nm; and a third LED configured to emit the electromagnetic radiation output between 300 and 430 nm. In various embodiments, a relative intensity output is controlled by blending the first electromagnetic radiation, the second electromagnetic radiation, and the third electromagnetic radiation to emit a target color from the lighting unit. The electromagnetic radiation output may be between 390 and 420 nm. The sanitization system may further comprise an air management system, the air management system including the external ROS generator.

A sanitization system for an aircraft is disclosed herein. The sanitization system may comprise: a lighting unit; an external reactive oxygen species (ROS) generator, a controller in operable communication with the lighting unit and the external ROS species generator, the controller operable to: command a light in the lighting unit to emit an electromagnetic radiation output between 300 and 430 nanometers ("nm"); command the external ROS generator to dispense a ROS into a cabin of the aircraft; and command the light and the external ROS generator to target a desired target area.

In various embodiments, the controller is further operable to determine the desired target area for bacterial or viral disinfection. The sanitization system may further comprise an air handling unit, the external ROS generator disposed in the air handling unit. The electromagnetic radiation output may be between 390 and 430 nm. The electromagnetic radiation output is about 405 nm. The lighting unit and the external ROS generator may be configured to disinfect a portion of the cabin in response to targeting the desired target area together.

An aircraft is disclosed herein. The aircraft may comprise: a cabin having a row of seats; a passenger service unit having a light assembly for the row of seats, the light assembly configured to emit an electromagnetic radiation output between 300 and 430 nanometers ("nm"); an external reactive oxygen species (ROS) generator configured to dispense an aerosolized ROS into the cabin proximate the row of seats, wherein a first direction of the electromagnetic radiation output is configured to intersect a second direction of the aerosolized ROS.

In various embodiments, the aerosolized ROS comprises one of hydrogen peroxide or ozone. The aircraft may comprise an air management system, the external ROS generator being integrated within the air management system. The air management system may include an air handling unit, the external ROS generator in fluid communication with the air management system. The electromagnetic radiation output may be between 390 and 430 nm. The electromagnetic radiation output may be about 405 nm.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIG. 6 illustrates a schematic flow chart diagram showing a controller method, in accordance with various embodiments.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Figure 1:
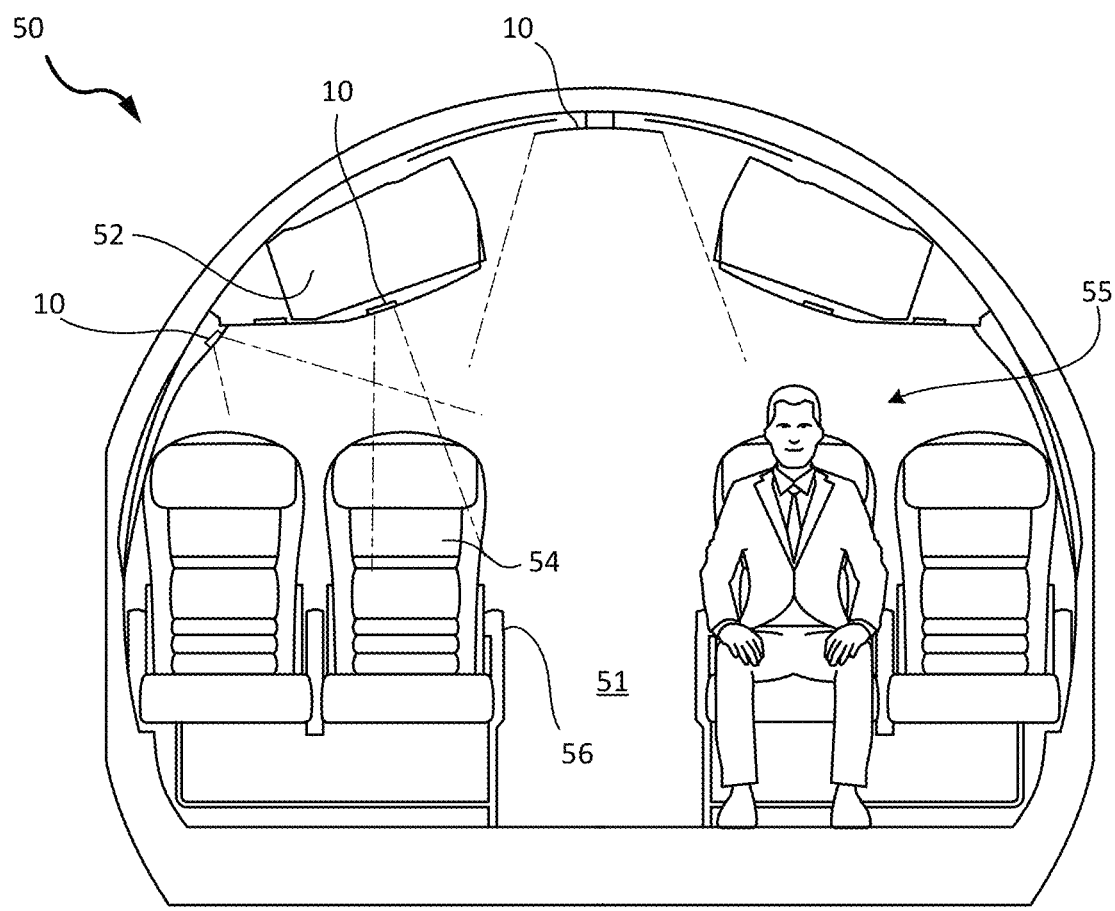
FIG. 1 illustrates a view of a cabin of an aircraft, in accordance with various embodiments.

In various embodiments, a 300-430 nm wavelength lighting system may kill bacteria and viruses through activation of Reactive Oxygen Species (ROS) which breaks down the bacteria and viruses. As described herein, a "wavelength" within a range may refer to a single wavelength within the wavelength range, or multiple wavelengths falling within the wavelength range. In various embodiments, bacteria have more internal ROS species than viruses, and thus a better response. Other applications demonstrate that the balance between Porphyrins and ROS may be augmented externally. In various embodiments, indoor environments (especially airplanes) have low naturally occurring ROS. Natural ROS is altitude dependent and external air intake will not have any natural ROS. Thus, in various embodiments, an aerosol ROS may be utilized to augment the virus killing behavior of a 405 nm wavelength, for instance, lighting system on an aircraft as illustrated in FIG. 1 attached. FIG. 1 illustrates an example of aerosol ROS to augment a virus killing behavior of light on an aircraft.

In various embodiments, lighting systems as disclosed herein may be applicable to any closed space where virus and bacteria may live. ROS could be on the intake air-line or in the cabin. $H_2O_2$ may be created from inert products, such as water and air. In various embodiments, an airplane lighting system may be used, as disclosed herein, as a wash lighting system to simulate the reaction. Porphyrins stimulate peak reaction is around 405 nm. In various embodiments, at a half-life of 10 ms, aerosol content of viral matter may be controlled on airplanes and augment a lighting system.

In various embodiments, by supplying a low, safe level of hydrogen peroxide ($H_2O_2$) to the environment, a reactive oxygen species (ROS), which attacks and disables bacteria and viruses externally, may be introduced. A 405 nm wavelength lighting system may have the ability to create ROS internally to the bacterial cell and disable it via porphyrin. The environment of $H_2O_2$ may be distributed either by the air management system, gasper or other discrete spraying/distribution elements. The lighting system would be full color cabin lighting and provide large amounts of 405 nm wavelength as part of its mix.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

In various embodiments, the various lighting systems 10 may be augmented with a reactive oxygen species (ROS). In various embodiments, by supplying a low, safe level of hydrogen peroxide ($H_2O_2$) into the cabin 51 of the aircraft 50, the ROS may be introduced and react with near ultraviolet light (300-430 nm) emitted by the various lighting systems 10. Although described herein with respect to hydrogen peroxide, the present disclosure is not limited in this regard. For example, any external reactive oxygen supply is within the scope of this disclosure, such as ozone, or the like. In various embodiments, reacting the ROS with the near ultraviolet light may have synergistic effects with respect to inactivation of a virus. In particular, ultraviolet light irradiation of spores of Bacillus subtilis in the presence of hydrogen peroxide produced a rapid kill which was up to 2000-fold greater than that produced by irradiation alone.

The synergy between an environment of $H_2O_2$ (effective externally) combined with the 405 nm (effective internally) may be superior to either alone. The combination may provide a new way of rapidly disinfecting the cabin without harmful UV and without strong chemicals (bleach, etc.). In various embodiments, other benefits are long term material stability, option of in-flight or overnight use and variable strength mixes. The system can be turned on and off intermittently where needed. Disinfecting of the various different regions of the aircraft may be undertaken in any appropriate manner (e.g., simultaneously, sequentially, or any combination thereof).

Figure 2:
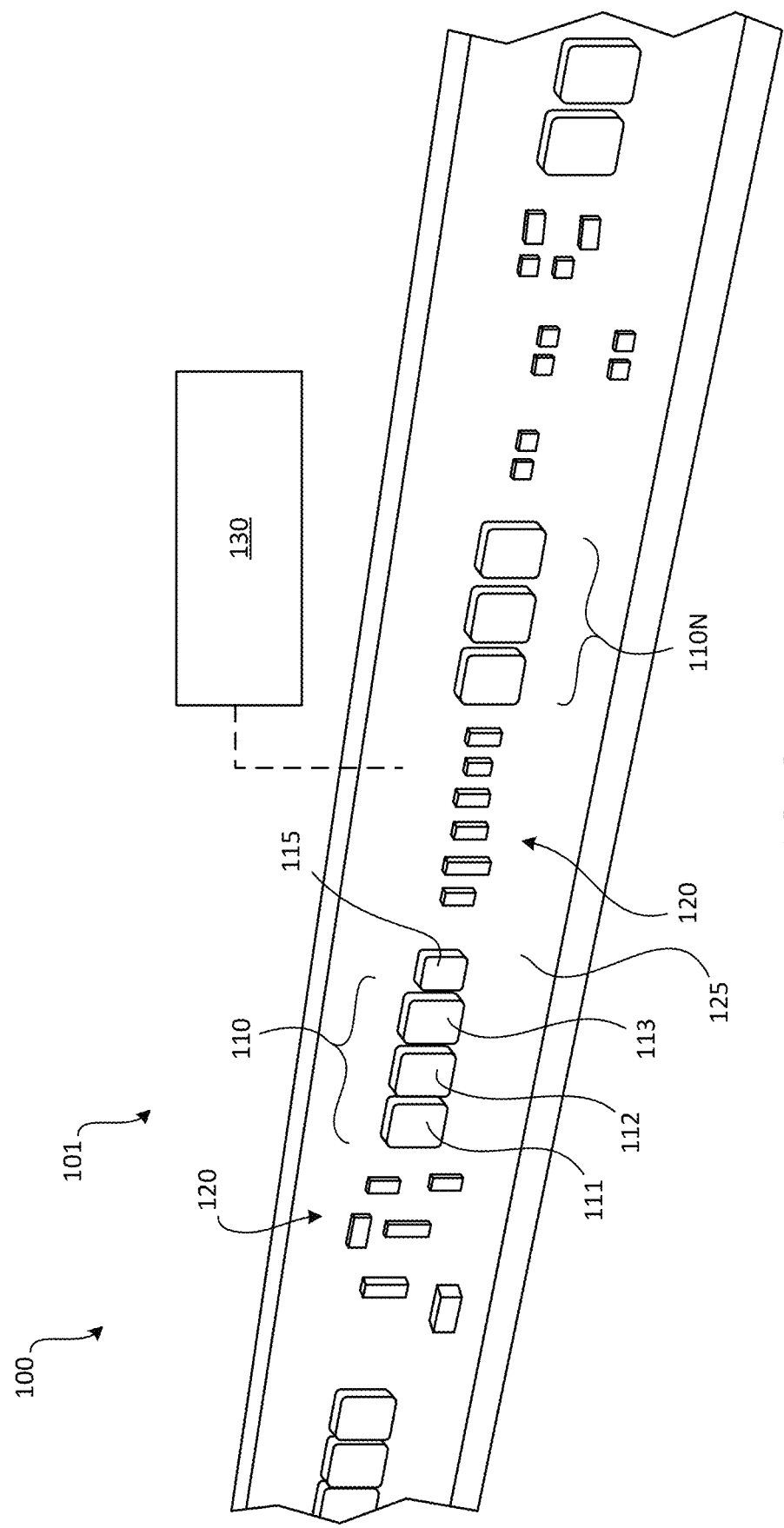
FIG. 2 illustrates a perspective view of a light system including at least one lighting unit, circuitry, and a controller, in accordance with various embodiments.

In various embodiments, and with reference to FIG. 2, a portion of a sanitization system 100 with a lighting system 101 is provided. The lighting system 101 may be one or more of the lighting systems 10 of the aircraft 50 from FIG. 1. The lighting system 101 generally includes a lighting unit 110 and circuitry 120, according to various embodiments. The sanitization system 100 includes the lighting system 101 and a controller 130. The controller 130 is in operable communication with the lighting system 101 and an ROS distribution system, as described further herein, and that also is part of the sanitization system 100. The lighting unit 110, according to various embodiments, includes a specific light-emitting diode ("LED") configured to emit electromagnetic radiation that is at least partially effective at inactivating and/or inhibiting pathogens. With this specific LED incorporated with other standard LEDs, the disinfecting electromagnetic radiation may be masked (i.e., blended) with the other electromagnetic radiation. Additional details pertaining to the lighting unit 110, the circuitry 120, and the controller 130 are provided below.

The term "lighting unit," as used herein, generally refers to an array of discrete LEDs that are controlled to blend their respective radiations to collectively produce a desired hue and intensity of electromagnetic radiation. In various embodiments, the lighting unit 110 includes a first LED 111 configured to emit first electromagnetic radiation having a first wavelength of between about 600 nanometers ("nm") and about 740 nm (e.g., red light), a second LED 112 configured to emit second electromagnetic radiation having a second wavelength of between about 500 nm and about 565 nm (e.g., green light), and a third LED 113 (e.g., the 'specific' LED mentioned above) configured to emit third electromagnetic radiation having a third wavelength between about 315 nm and about 430 nm. In various embodiments, the third wavelength is between about 390 nm and about 420 nm. In various embodiments, the third wavelength is about 405 nm. As used in this context only, the term "about" refers to plus or minus 5 nm. Thus, the third LED 113 may emit "long-wave" ultraviolet light, commonly referred to as "UV-A" light, and this third LED 113 may replace a conventional blue LED. This type UV-A light may facilitate a degree of pathogen inactivity and/or inhibition over a conventional blue LED, and thus is referred to herein as "disinfecting electromagnetic radiation," while still being safe for humans. Pathogens may refer to bacteria, viruses, fungal spores, and other microorganisms. In various embodiments, the lighting unit 110 may include more than these three LEDs. For example, the lighting unit may include 4, 5, 6, 7, or 8 LEDs, and these additional LEDs may be other colors, such as amber, cyan, etc.

Figure 3:
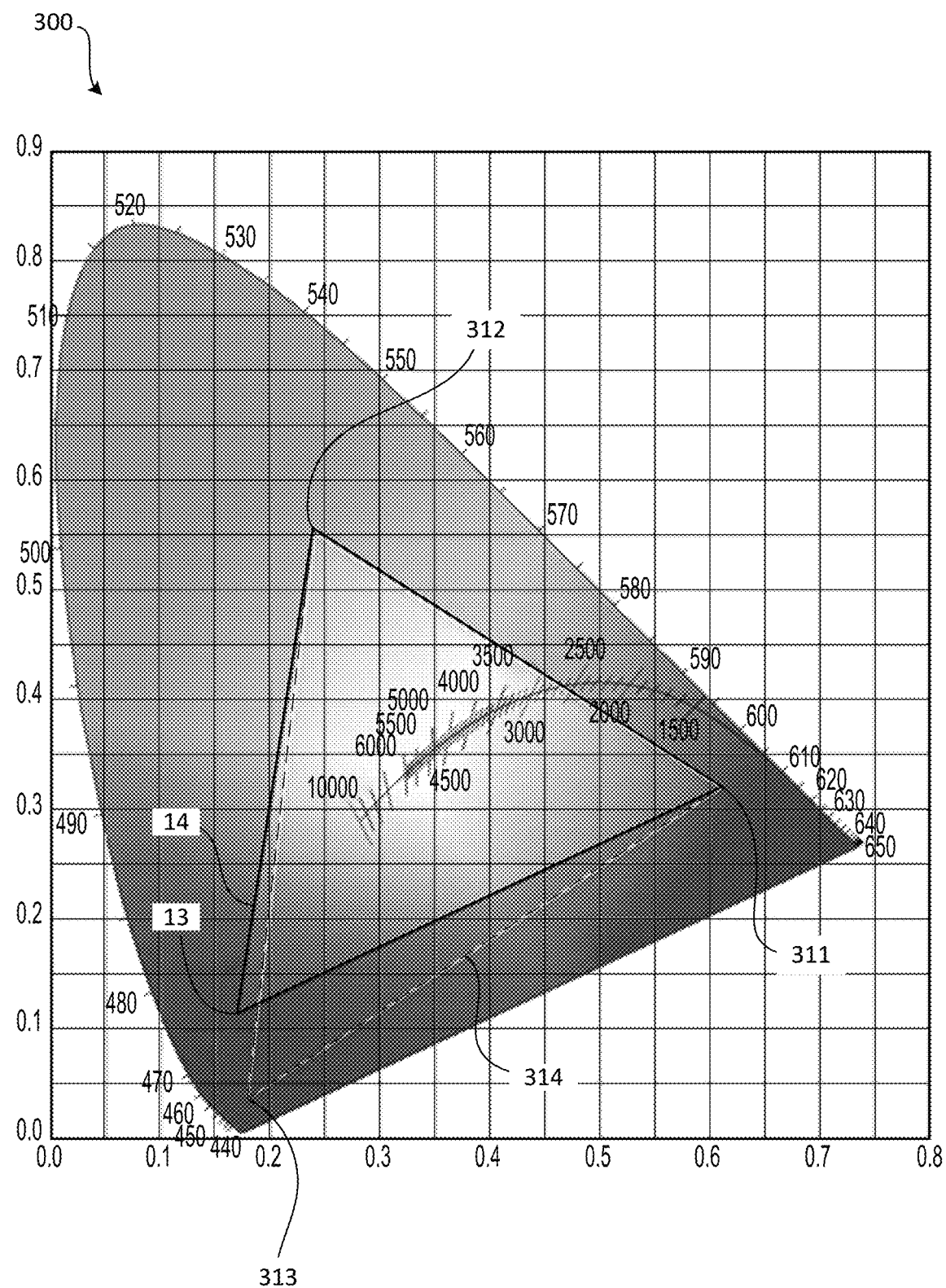
FIG. 3 is a color space chromaticity diagram from the International Commission on Illumination ("CIE"), commonly referred to as a CIE 1931 system diagram, showing various triangular color gamuts, utilized by various embodiments.
Figure 4:
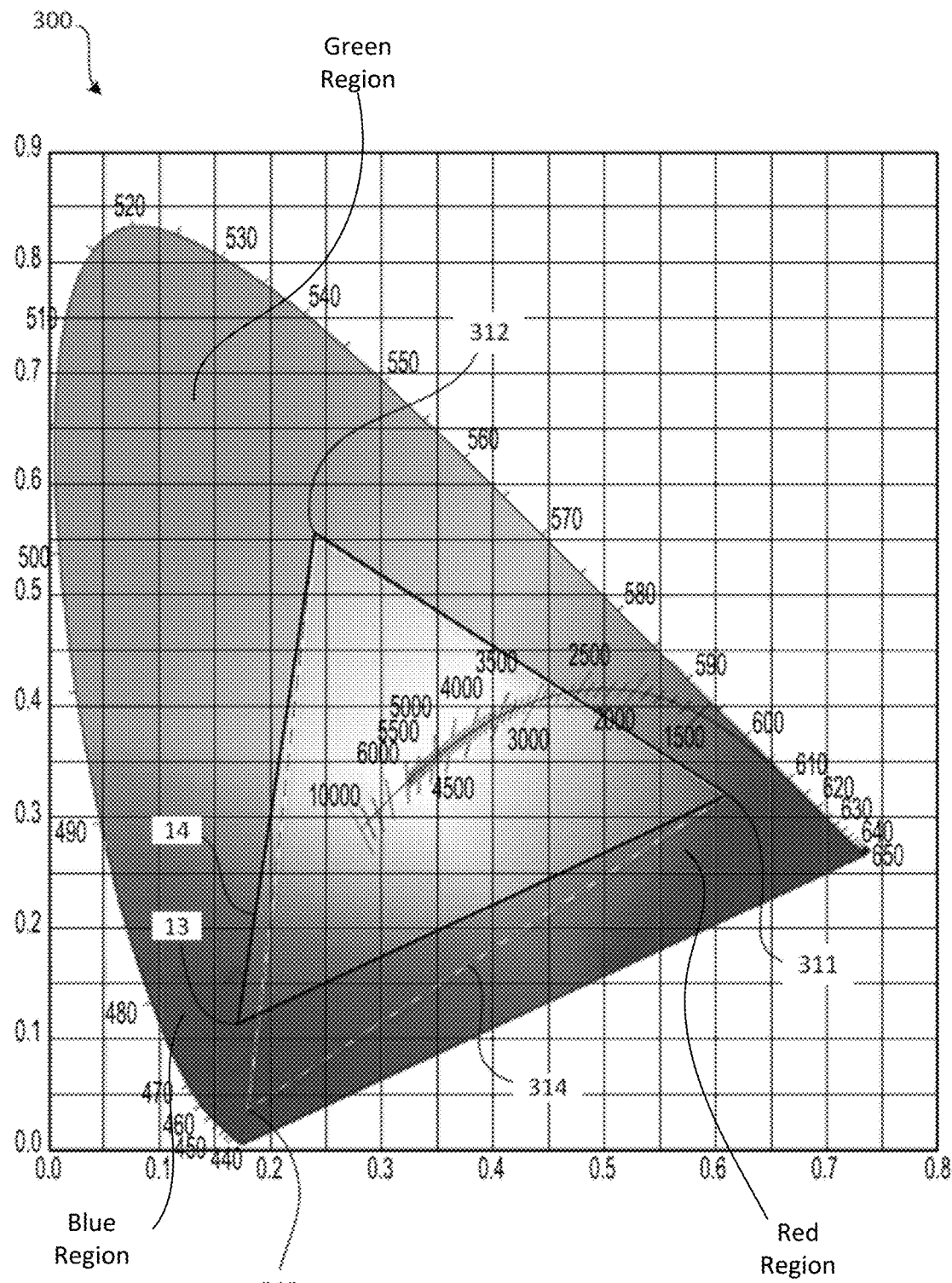
FIG. 4 is a black and white representation of the color space chromaticity diagram of FIG. 3, with various color regions labeled, in accordance with various embodiments.

In various embodiments, and with momentary reference to FIG. 3, a color space chromaticity diagram from the International Commission on Illumination ("CIE"), commonly referred to as a CIE 1931 system diagram 300, is provided. FIG. 4 is a black and white representation of FIG. 3 with various regions of the CIE 1931 system diagram 300 labeled with their respective colors. That is, FIG. 4 is labeled with a red region, a green region, and a blue region. The CIE 1931 system diagram 300 shows a conventional color gamut 14 in which a conventional blue LED 13 is utilized in a conventional lighting unit, and the CIE 1931 system diagram 300 also shows a disinfecting color gamut 314 provided by replacing the conventional blue LED 13 with a specific LED 313 configured to emit disinfecting electromagnetic radiation. Thus, both the conventional color gamut 14 and the disinfecting color gamut 314 may be formed of a first LED 311 and a second LED 312, which may be comparable to the first LED 111 and the second LED 112, respectively referenced above, but the disinfecting color gamut 314 includes LED 313 configured to emit UV-A light as opposed to "blue" light. The shifted, disinfecting color gamut 314 still provides for the collective radiation of the three LEDs 311, 312, 313 to be tuned based on desired color output, as described in greater detail below. That is, the lighting unit 110 may still be controlled to create different lighting schemes within color gamut 314 while including (e.g., masking) UV-A radiation, such as a purple branding color output, a white color output, or the like. In various embodiments, if the lighting unit has more than 3 LEDs, the color gamut may be further expanded (e.g., may be referred to as a hyper gamut and may comprise, for example 6 LEDs). Thus, the lighting unit 110 disclosed herein generally replaces a conventional "blue" light with the UV-A light.

Returning to reference FIG. 2, the circuitry 120 of the lighting system 101 may include a circuit board 125 and may generally include various integrated circuit components which may carry out a variety of functions under the control of the controller 130. In various embodiments, the combination of the lighting unit 110 and the circuitry 120 is referred to as a lighting assembly, and the lighting assembly is configured to be driven/controlled by the controller 130, as described in greater detail below. The particular implementations shown and described herein are illustrative examples of an LED lighting assembly and are thus not intended to otherwise limit the scope of the present disclosure in any way. For the sake of brevity, conventional electronics or other components of the circuitry (such as power supplies and power modulators) may not be described in detail herein. The circuitry 120 is electrically coupled to the lighting unit 110 to supply respective driving signals to each of the LEDs 111, 112, 113. In various embodiments, the lighting unit 110 may include additional LEDs, such as a white LED 115. In various embodiments, the lighting unit consists of only the three LEDs 111, 112, 113 described above, and thus may not include other LEDs. The lighting unit 110 may be replicated/repeated along a strip of circuit board 125. In various embodiments, the circuitry 120 and/or the circuit board 125 includes a fluorescence inhibiting coating that is configured to decrease fluorescence of the circuit board in response to the UV-A radiation. In various embodiments, the lighting unit 110 may include a diffuser lens (or diffuser lenses) covering the LEDs 111, 112, 113, and these lens(es) may comprise a glass material, a polymethyl methacrylate material, and/or a polyamide material, among others. In various embodiments, these lens(es) are not made from polycarbonate materials, as UV-A radiation may not transmit well through such materials.

Figure 5:
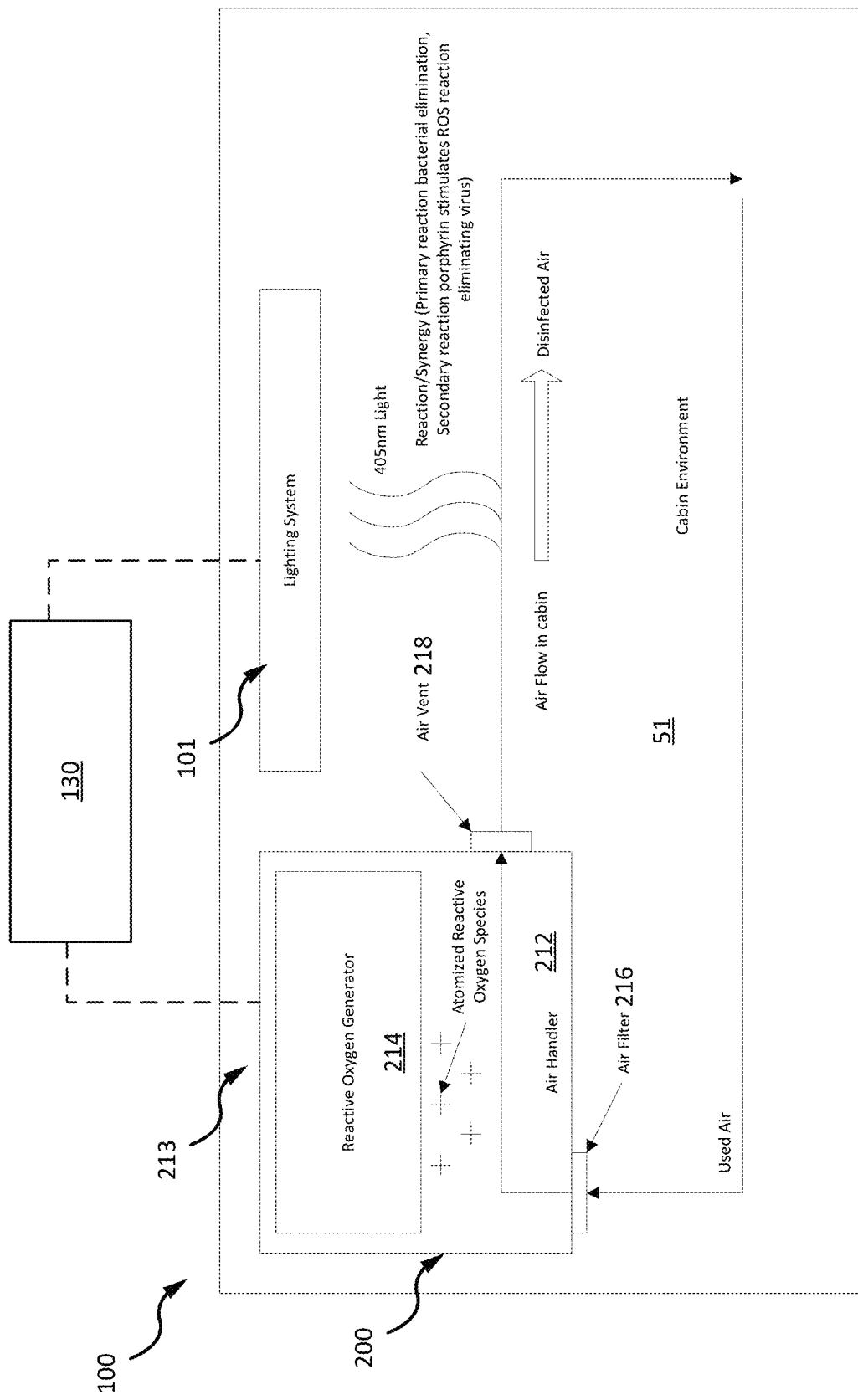
FIG. 5 illustrates a schematic view of a sanitization system for a cabin of an aircraft, in accordance with various embodiments.

Referring now to FIG. 5, a schematic view of a sanitization system 100 with the lighting system 101 from FIG. 2 is illustrated, in accordance with various embodiments. In various embodiments, the sanitization system 100 includes the lighting system 101 and an ROS distribution system 213. The ROS distribution system 213 may be integrated into a cabin air management system 210, in accordance with various embodiments. Although illustrated as being integrated in a cabin air management system 210, the present disclosure is not limited in this regard. For example, the ROS distribution system 213 may be an independent component from a cabin air management system, in accordance with various embodiments.

In various embodiments, the cabin air management system 210 includes an air handler 212. In various embodiments, the air handler 212 is configured to regulate and circulate air as a part of the cabin air management system 210. In various embodiments, the air handler 212 may include a blower, heating or cooling elements, filter racks or chambers, sound attenuators, dampers, or the like. In various embodiments, the cabin air management system 210 further comprises an air filter 216 and an air vent 218. In various embodiments, the air filter 216 is configured as an air inlet from the cabin 51 to the air handler 212, and the air vent 218 is configured as an air outlet from the air handler 212 to the cabin 51.

In various embodiments, the ROS distribution system 213 comprises a reactive oxygen (ROS) generator 214. The ROS generator 214 is configured to generate an atomized ROS species, in accordance with various embodiments. For example, the ROS generator 214 may be configured to generate atomized, or aerosolized, hydrogen peroxide, atomized, or aerosolized, ozone, or the like. Although described as being aerosolized, the ROS generator 214 is not limited in this regard. For example, the ROS generator 214 may be configured to generate the respective ROS via a flat fan, a solid stream, a full cone, a hollow cone, and/or a mist, in accordance with various embodiments.

In various embodiments, the ROS generator 214 dispenses the respective ROS internally within the air handler 212 and the air handler distributes the ROS into the cabin 51. In various embodiments, the ROS may be dispensed directly into the cabin 51, in accordance with various embodiments. In this regard, the controller 130 may be configured to align a spray of ROS generator 214 and a light in the lighting system 101 to intersect at a desired disinfected air/surface in the cabin 51. Similarly, when the ROS generator 214 is integrated in the air handler 212, the controller 130 may be configured to direct air released from the air vent 218 and a light in the lighting system 101 to intersect at a desired disinfected air/surface in the cabin 51.

In various embodiments, the controller 130 is operable to control and/or modulate an ROS concentration distributed into the cabin 51. In this regard, the sanitization system may maintain a predetermined concentration of ROS, in accordance with various embodiments. For example, the controller 130 may be configured to modulate the ROS generator 214 continuously to maintain the predetermined concentration.

In various embodiments, and with combined reference to FIGS. 2 and 5, the controller 130 of the sanitization system 100 may be affixed/integrated into the circuitry 120 of light system 101 or the controller 130 may be integrated into computer systems onboard an aircraft. The controller 130 in FIG. 2 is shown schematically, and thus the size, position, and orientation of the controller may be different than what is depicted in FIG. 2. In various embodiments, the controller 130 comprises a processor. In various embodiments, the controller 130 is implemented in a single processor. In various embodiments, the controller 130 may be implemented as and may include one or more processors and/or one or more tangible, non-transitory memories and be capable of implementing logic. Each processor can be a general purpose processor, a digital signal processor (DSP), an application specific integrated circuit (ASIC), a field programmable gate array (FPGA) or other programmable logic device, discrete gate or transistor logic, discrete hardware components, or any combination thereof. The controller 130 may comprise a processor configured to implement various logical operations in response to execution of instructions, for example, instructions stored on a non-transitory, tangible, computer-readable medium (i.e., the memory) configured to communicate with the controller 130. Furthermore, any number of conventional techniques for electronics configuration, signal processing and/or control, data processing and the like may be employed. Also, the processes, functions, and instructions may can include software routines in conjunction with processors, etc.

System program instructions and/or controller instructions may be loaded onto a non-transitory, tangible computer-readable medium having instructions stored thereon that, in response to execution by the processor, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory of the controller 130 may be configured to perform various operations. The schematic flow chart diagram of FIG. 6 includes a controller method 600 that the processor of the controller 130 may perform, in accordance with various embodiments. Generally, the controller 130 is operably (e.g., electrically or wirelessly through a network) coupled to the circuitry 120 and is configured to control, by the processor, the relative intensity outputs of the respective LEDs 111, 112, 113 of the lighting unit 110, a direction of the respective LEDs 111, 112, 113, a dosage amount of an ROS from ROS Generator 214, and/or a direction of air from ROS generator 214 or air handler 212, according to various embodiments.

Referring now to FIG. 6, a method of sanitizing a target area of an aircraft cabin is illustrated, in accordance with various embodiments. In various embodiments, the method 600 may comprise determining, by the processor, a desired target area for bacterial or viral disinfection (step 602). In various embodiments, the desired target may be any area in a cabin of an aircraft, such as a tray table, a passenger seat, an arm rest, a window, or the like. In various embodiments, the desired target may be determined in response to the processor receiving an indication that a pathogen has been released (e.g., via a microphone sensor detecting a sneeze, or the like).

The method 600 may further comprise commanding, by a processor, a light in a light system to emit an electromagnetic radiation having a wavelength between 300 nm and 430 nm (step 604). In various embodiments, the light in accordance with step 602 may create ROS internally to a bacterial cell and disable the bacterial cell via porphyrin.

In various embodiments, the method 600 may further comprise commanding, by the processor, a reactive oxygen species (ROS) to be dispensed into an aircraft cabin (step 606). In various embodiments, the ROS may comprise hydrogen peroxide, ozone, or the like. In various embodiments, the dispensed ROS may be configured to attack and disable bacteria and viruses externally, resulting in a synergistic inactivation of a bacteria or virus (e.g., a 2,000 fold increase in virus inactivation relative to UV only or hydrogen peroxide only as described previously herein).

In various embodiments, the method 600 further comprises commanding, by the processor, the light and the ROS to target the desired target area in combination (step 608). In various embodiments, targeting the desired target area may result in a synergistic inactivation of a bacteria or virus, as described previously herein. The combination of the light and the ROS may vastly increase inactivation relative to only an external ROS or an ultraviolet light.

In various embodiments, the method 600 further comprises receiving, by the processor, an ROS concentration within the cabin (step 610). The ROS concentration may be received from the ROS generator or a sensor, in accordance with various embodiments. For example, the ROS generator may be configured to track an amount of ROS released into the cabin and send the amount to the controller for processing. In various embodiments, a sensor may be configured to measure a concentration of the ROS and send the concentration amount to the processor.

In various embodiments, the method 600 further comprises modulating, by the processor and through the ROS generator, an ROS concentration released into the cabin (step 612). In various embodiments, modulating the ROS concentration may maintain a concentration of ROS in the cabin of the aircraft below a threshold concentration of ROS.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization system for an aircraft cabin, the sanitization system comprising:
   a passenger service unit comprising a light system, the light system comprising:
      a first light-emitting diode (LED) configured to emit a first electromagnetic radiation output between 600 and 740 nm,
      a second LED configured to emit a second electromagnetic radiation output between 500 and 565 nm, and
      a third LED configured to emit a third electromagnetic radiation output between 390 and 420 nm, wherein a relative intensity output is controlled by blending the first electromagnetic radiation output, the second electromagnetic radiation output, and the third electromagnetic radiation output to emit a target color from the light system; and
   an external reactive oxygen species (ROS) generator configured to be in fluid communication with the aircraft cabin, wherein the sanitization system is configured to disinfect a target area of the aircraft cabin by targeting the target area with the third electromagnetic radiation output and the external ROS generator, wherein the light system is a full color lighting system.

2. The sanitization system of claim 1, wherein an ROS produced by the external ROS generator is hydrogen peroxide or ozone.

3. The sanitization system of claim 2, wherein the ROS is an aerosolized hydrogen peroxide.

4. The sanitization system of claim 1, further comprising an air handler configured to be in fluid communication with the aircraft cabin, wherein the external ROS generator is in fluid communication with the air handler.

5. The sanitization system of claim 1, further comprising an air management system, the air management system including the external ROS generator.

6. A sanitization system for an aircraft, the sanitization system comprising:
   a passenger service unit comprising a lighting unit, the lighting unit including a first light, a second light, and a third light;

an external reactive oxygen species (ROS) generator;
a controller in operable communication with the lighting unit and the external ROS generator, the controller operable to:
  controlling a relative intensity output of the lighting unit by blending a first electromagnetic radiation output of the first light of the lighting unit, a second electromagnetic radiation output of the second light of the lighting unit, and a third electromagnetic radiation output of the third light of the lighting unit to emit a target color from the lighting unit;
  command the first light in the lighting unit to emit an electromagnetic radiation output between 390 nanometers ("nm") and 430 nm;
  command the external ROS generator to dispense a ROS into a cabin of the aircraft; and
  command the first light and the external ROS generator to target a desired target area, wherein a combination of the external ROS generator and the electromagnetic radiation output produce a synergistic effect with respect to inactivation of a virus.

7. The sanitization system of claim 6, wherein the controller is further operable to determine the desired target area for bacterial or viral disinfection.

8. The sanitization system of claim 6, further comprising an air handling unit, the external ROS generator disposed in the air handling unit.

9. The sanitization system of claim 6, wherein the electromagnetic radiation output is about 405 nm.

10. An aircraft cabin and the sanitization system of claim 6, wherein the lighting unit and the external ROS generator are configured to disinfect a portion of the aircraft in response to targeting the desired target area together.

11. The sanitization system of claim 6, wherein:
  the second light is configured to emit the first electromagnetic radiation output between 600 and 740 nm, and
  the third light is configured to emit the second electromagnetic radiation output between 500 and 565 nm.

12. An aircraft, comprising:
a cabin having a row of seats;
a passenger service unit having a light assembly for the row of seats, the light assembly including a first light configured to emit a first electromagnetic radiation output between 390 and 430 nanometers ("nm"), wherein a relative intensity output is controlled by blending the first electromagnetic radiation output, a second electromagnetic radiation output from a second light of the light assembly, and a third electromagnetic radiation output of a third light of the light assembly to emit a target color from the light assembly;
an external reactive oxygen species (ROS) generator configured to dispense an aerosolized ROS into the cabin proximate the row of seats, wherein a first direction of the first electromagnetic radiation output is configured to intersect a second direction of the aerosolized ROS, wherein a combination of the external ROS generator and the first electromagnetic radiation output produce a synergistic effect with respect to inactivation of a virus.

13. The aircraft of claim 12, wherein the aerosolized ROS comprises one of hydrogen peroxide or ozone.

14. The aircraft of claim 12, further comprising an air management system, the external ROS generator being integrated within the air management system.

15. The aircraft of claim 14, wherein the air management system includes an air handling unit, the external ROS generator in fluid communication with the air management system.

16. The aircraft of claim 12, wherein the first electromagnetic radiation output is about 405 nm.

17. The aircraft of claim 12, wherein:
  the second light is configured to emit the second electromagnetic radiation output between 600 and 740 nm, and
  the third light configured to emit the third electromagnetic radiation output between 500 and 565 nm.

* * * * *